United States Patent
Jutte et al.

(10) Patent No.: US 9,457,431 B2
(45) Date of Patent: Oct. 4, 2016

(54) CUTTING HEAD FOR A DEVICE FOR CUTTING HAIR

(71) Applicant: KONINKLIJKE PHILIPS N.V., Eindhoven (NL)

(72) Inventors: Petrus Theodorus Jutte, Eindhoven (NL); Bastiaan Wilhelmus Maria Moeskops, Eindhoven (NL); Mark Thomas Johnson, Eindhoven (NL); James Howard Coombs, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/401,690

(22) PCT Filed: May 17, 2013

(86) PCT No.: PCT/IB2013/054055
§ 371 (c)(1),
(2) Date: Nov. 17, 2014

(87) PCT Pub. No.: WO2013/175373
PCT Pub. Date: Nov. 28, 2013

(65) Prior Publication Data
US 2015/0101201 A1    Apr. 16, 2015

Related U.S. Application Data

(60) Provisional application No. 61/649,985, filed on May 22, 2012, provisional application No. 61/774,634, filed on Mar. 8, 2013.

(51) Int. Cl.
*A61B 18/20*    (2006.01)
*B23K 26/02*    (2014.01)
(Continued)

(52) U.S. Cl.
CPC ........... *B23K 26/4035* (2013.01); *A61B 18/20* (2013.01); *A61B 18/203* (2013.01);
(Continued)

(58) Field of Classification Search
CPC ...... B23K 26/00; B23K 26/02; B23K 26/38; A61B 18/20; B26F 3/16
USPC ............. 606/9; 607/89; 219/121.67; 30/140; 372/50.12, 101, 109
See application file for complete search history.

(56) References Cited

U.S. PATENT DOCUMENTS 5,065,515 A * 11/1991 Iderosa ................ A61B 18/203
                                                      132/200
5,472,046 A    12/1995 Brucher
(Continued)

FOREIGN PATENT DOCUMENTS

JP         5509028 A    12/1993
JP     2005177788 A     7/2005
(Continued)

OTHER PUBLICATIONS

Doric Lenses Inc., "Fiber-coupling of Laser Diode" pp. 1-4, 2007.

*Primary Examiner* — Samuel M Heinrich (57) ABSTRACT

The present application relates to a cutting head (1) for a device for cutting hair. The cutting head has an optical system (3) which directs a laser beam (7) across a cutting zone (8) in the cutting head. The laser beam has a fast and a slow axis. The optical system has a focus lens (6) configured to form a first focal point (11) of the laser beam in the cutting zone. In one embodiment, the optical system (3) also has a focusing element (15) which refocuses the laser beam to form a second focal point (16) of the laser beam in the cutting zone. In another embodiment, the focus lens forms a focal length of the laser beam in the cutting zone along its fast axis which is greater than a focal length of the laser beam in the cutting zone along its slow axis.

15 Claims, 4 Drawing Sheets (51) Int. Cl.
    *B23K 26/38* (2014.01)
    *B26F 3/16* (2006.01)
    *B23K 26/40* (2014.01)
    *B26B 19/00* (2006.01)
    *B23K 26/00* (2014.01)
    *B23K 26/06* (2014.01)
    *B23K 26/073* (2006.01)
    *A61B 18/00* (2006.01)
    *A61N 5/06* (2006.01)
    *A61N 5/067* (2006.01)

(52) U.S. Cl.
    CPC ........... *B23K26/0096* (2013.01); *B23K 26/02* (2013.01); *B23K 26/0648* (2013.01); *B23K 26/0736* (2013.01); *B23K 26/38* (2013.01); *B23K 26/402* (2013.01); *B26B 19/00* (2013.01); *B26F 3/16* (2013.01); *A61B 2018/00476* (2013.01); *A61N 2005/067* (2013.01); *A61N 2005/0663* (2013.01); *A61N 2005/0665* (2013.01); *B23K 2203/32* (2015.10); *B23K 2203/38* (2015.10)

(56) References Cited

U.S. PATENT DOCUMENTS

| | | | |
|---|---|---|---|
| 5,986,744 A | 11/1999 | Kudo | |
| 6,301,059 B1 | 10/2001 | Huang | |
| 6,758,845 B1* | 7/2004 | Weckwerth | A61B 18/203 128/898 |
| 9,017,322 B2* | 4/2015 | Gustavsson | A61B 18/203 606/36 |
| 2005/0177139 A1 | 8/2005 | Yamazaki | |
| 2012/0092740 A1 | 4/2012 | Kimura | |

FOREIGN PATENT DOCUMENTS

| | | |
|---|---|---|
| JP | 2006122988 A | 5/2006 |
| JP | 2010173316 S | 8/2010 |
| WO | 9533600 A1 | 12/1995 |
| WO | 9622741 A1 | 8/1996 |
| WO | 2006004135 A1 | 1/2006 |
| WO | 2008070851 A2 | 6/2008 |
| WO | 2008112723 A1 | 9/2008 |
| WO | 2013068932 A1 | 5/2013 |

* cited by examiner

CUTTING HEAD FOR A DEVICE FOR CUTTING HAIR

This application is the U.S. National Phase application under 35 U.S.C. §371 of International Application No. PCT/IB2013/054055, filed on May 17, 2013, which claims the benefit of U.S. Provisional Application No. 61/649,985 filed on May 22, 2012 and U.S. Provisional Application No. 61/774,634 filed on Mar. 8, 2013. These applications are hereby incorporated by reference herein.

FIELD OF THE INVENTION

The present application relates to a cutting head for a device for cutting hair.

BACKGROUND OF THE INVENTION

It is known to provide a shaver or razor that relies on a laser for cutting hair rather than an arrangement of cutting blades. Shavers without blades have fewer moving parts and so wear is reduced, which provides an advantage over mechanical shavers. Furthermore, the use of a laser can reduce skin irritation as there are no sharp objects that contact the skin surface. Laser shavers work by optical absorption, also known as laser ablation, in which hair exposed to a laser beam absorbs the energy of the beam, causing it to be vaporised and/or severed.

Shaving performance is typically measured by two criteria closeness of shave and irritation of the skin. Therefore, a good performing shaver should minimise the remaining hair length by positioning the laser as close as possible to the skin. However, this may cause more skin irritation if heat and energy from the laser is incident on the skin. It is necessary to protect the skin from contact with the laser beam to avoid damaging or irritating the skin being shaved. Hair trimmers or groomers are used to trim hair to a constant length, so although closeness is not a major performance factor, uniformity of remaining hair length is desirable.

It is known, for example from WO 95/33600, to generate a laser beam that is positioned parallel to the skin and perpendicular to the stroke direction to cut hairs as the shaver is moved over the skin. However, Gaussian theory dictates that laser beams have a natural intensity variation along their length. Beams will have a focal point where the laser beam has maximum intensity (power per unit area) and minimum width, meaning the focal point is the most effective part of the laser beam for severing hair by optical absorption. On the other hand, parts of the laser beam furthest from the focal point will have a larger width and therefore a more distributed intensity and will not be as effective at severing hair because the energy of the laser beam is incident over a larger area of hair. Therefore, there is a variation in hair severing performance along the optical axis of a laser beam and this may result in uneven hair severing and non-uniform closeness. Moreover, the power density distribution in each position over a cutting zone in which hairs are received is not always sufficient to cut hair. Due to the natural divergence of Gaussian laser beams it is impossible to achieve a uniform beam thickness along an optical axis.

SUMMARY OF THE INVENTION

It is an object of the invention to provide a cutting head for a device for cutting hair which substantially alleviates or overcomes the problems mentioned above, amongst others.

According to the present invention, there is provided a cutting head for a device for cutting hair, comprising an optical system configured to direct a laser beam having a fast axis and a slow axis across a cutting zone in the cutting head, the optical system comprising a focus lens configured to form a first focal point of the laser beam in the cutting zone, and a focusing element configured to form a second focal point of the laser beam in the cutting zone.

Therefore, it is possible to refocus the laser beam and create another effective cutting area. This means that the power density can be maximised along a greater length of the laser beam, and so it is possible to increase the length of the cutting zone without reducing the effectiveness of the cutting head, or increasing the required power of the laser beam.

The focusing element may be in the cutting zone.

This means that it is possible to extend the length of the cutting zone by extending the effective cutting area of the laser in the cutting zone.

The focusing element may be disposed in a middle section of the cutting zone. Therefore, it is possible to provide a symmetrical cutting arrangement across the length of the cutting zone. That is, it is possible for the power density distribution of the laser beam to be symmetrical on opposing sides of the focusing element, and therefore on each side of the cutting zone.

The focusing element may be a refractive lens. With this arrangement, it is possible to refocus the laser beam without affecting its path through the cutting zone.

The focusing element may a reflective lens. With this arrangement, it is possible to refocus the laser beam and reflect the laser beam back across the, or a section of the, cutting zone.

The focusing element is a spherical lens. Therefore, it is possible to refocus the laser beam along its fast and slow axes.

The focusing element may be a cylindrical lens. Therefore, more than one laser beam or sections of a laser beam may be refocused by the one focusing element.

The focusing element may be configured to refocus a laser beam along its fast axis only.

The focusing element may be configured to focus at least two laser beams.

The focus lens may be configured to form a focal length of the laser beam in the cutting zone along the fast axis which is different to a focal length of the laser beam in the cutting zone along the slow axis. The focal length along the slow axis may be greater than the focal length along the fast axis.

The focus lens may be configured to form a focal point of the laser beam along its fast axis which is offset from a focal point of the laser beam along its slow axis.

The focus lens and the focusing element may be spaced from each other so that the focal point of the laser beam along the slow axis coincides with the focusing element.

With this arrangement the power density and therefore the cutting action of the laser beam along the length of the cutting zone is symmetrical. That is, the beam width along both the slow and fast axes is symmetrical on opposing sides of the focusing element and therefore on each side of the cutting zone. This aids a uniform cutting action along the length of the cutting zone.

The focus lens may be configured to form the focal length of the laser beam along the fast axis which is greater than the focal length of the laser beam along the slow axis.

This provides a laser beam in the cutting zone which has a minimized numerical aperture along its fast axis and a high numerical aperture along its slow axis. Therefore, the power density of the laser beam is maximised along a greater distance, and so the effective cutting area of the laser beam is increased.

The focus lens may be configured so that a focal point of the laser beam along the fast axis coincides with the focal point of the laser beam along the slow axis.

This means that the power density and therefore the cutting action of the laser beam along the length of the cutting zone is symmetrical.

The focusing element may be a first focusing element, and the cutting head may further comprise a second focusing element configured to refocus the laser beam along its fast and/or slow axis.

Therefore, it is possible to form another effective cutting area of the laser beam in the cutting zone. This means that the length of the cutting zone in which an effective cutting area is formed can be maximised.

According to another aspect of the present invention, there is provided a device for cutting hair comprising a cutting head according to any of claims 1 to 9.

According to another aspect of the present invention, there is provided a cutting head for a device for cutting hair, comprising an optical system configured to direct a laser beam having a fast axis and a slow axis across a cutting zone in the cutting head, the optical system comprising a focus lens configured to form a focal length of the laser beam in the cutting zone along its fast axis which is greater than a focal length of the laser beam in the cutting zone along its slow axis.

This provides a laser beam in the cutting zone which has a minimized numerical aperture along its fast axis and a high numerical aperture along its slow axis. Therefore, the power density of the laser beam is maximised along a greater distance, and so the effective cutting area of the laser beam is increased.

The focal length of the laser beam along the fast axis may be at least double the focal length of the laser beam along the slow axis.

The focus lens may be configured so that a focal point of the laser beam along its fast axis coincides with a focal point of the laser beam along its slow axis.

This means that the cutting action along the length of the cutting zone is able to be symmetrical.

The focus lens may comprise a first focus lens portion configured to focus the laser beam along its fast axis and a second focus lens portion configured to focus the laser beam along its slow axis.

With this arrangement it is straightforward to provide a focus lens which forms different focal lengths of a laser beam along its fast axis and its slow axis. Furthermore, it is possible to easily determine the desired spacing between the focal points of the laser beam along its fast and slow axes.

The first focus lens portion may be a cylindrical lens. This means that the first focus lens portion focuses the laser beam along its fast axis only. By using a cylindrical lens it is possible to focus the laser beam along one axis, without focusing the laser beam along another axis.

The second focus lens portion may be a cylindrical lens. This means that the second focus lens portion focuses the laser beam along its slow axis only.

The optical system may further comprise a collimating lens, the first focus lens portion and the collimating lens being integrally formed.

This means that the number of components may be minimised. Therefore, the ease of manufacture is maximised.

The cutting head may further comprise a focusing element configured to form a second focal point along the slow axis and/or the fast axis of the laser beam in the cutting zone.

With this arrangement it is possible to maximise the effective cutting area of the laser beam, and therefore maximise the length of the cutting zone, due to the focusing element refocusing the laser beam incident on it.

The optical system may further comprise a first reflective element to direct the laser beam across the cutting zone.

The optical system may further comprise a second reflective element disposed on an opposite side of the cutting zone to the first reflective element to direct the laser beam away from the cutting zone.

In another embodiment, the optical system may further comprise a second reflective element disposed on an opposite side of the cutting zone to the first reflective element which is configured to reflect the laser beam back across the cutting zone.

The one or more focusing elements may be located either before or after such a reflective or refractive element.

This provides a second cutting section of the laser beam that passes through the cutting zone, therefore improving the cutting performance of the shaver.

According to another aspect of the present invention, there is provided a device for cutting hair comprising a cutting head according to any of claims 10 to 15.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
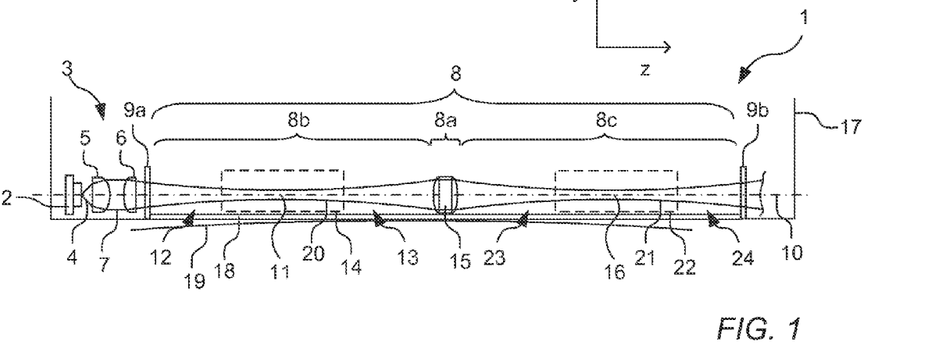
FIG. 1 shows a schematic side view of a cutting head for a device for cutting hair.

FIG. 1 shows a schematic diagram of a head unit 1 for a device for cutting hair. The head unit 1 forms a cutting head of a laser shaver. The head unit 1 comprises a laser generator 2, acting as a laser source, and an optical system 3. The laser generator 2 in the present arrangement is a diode. The laser generator 2 emits a laser beam 4. The laser beam 4 follows an optical path from the laser generator 2 in the head unit 1.

In the present arrangement, the emitted laser beam 4 is a multi-transverse-mode blue diode laser. The wavelength of the emitted laser beam 4 is about 450 nm. The power of the emitted laser beam 4 is in the order of magnitude of 3 W. However, it will be understood that characteristics of the laser beam may be varied.

The emitted laser beam 4 is directed towards the optical system 3. The optical system 3 has a collimating lens 5 and a focus lens 6. The laser beam 4 is directed towards the collimating lens 5. The collimating lens 5 reduces or eliminates the divergence of the beam. The collimated section or path 7 of the beam 4 is then focused by the focus lens 6 to cause the beam 4 to converge.

The head unit 1 has a cutting zone 8 in which hairs are received to be cut. A first window 9a is disposed between the cutting zone 8 and the focus lens 6. A second window 9b is disposed at the other end of the cutting zone 8 to the first window 9a. The second window 9b is disposed between the cutting zone 8 and an energy dissipater or similar device (not shown). The laser beam 4 travels through the cutting zone and is dissipated by the energy dissipater. The energy dissipater or similar device prevents damage being caused by the energy of the remaining laser beam 4.

The windows 9a, 9b are disposed to protect the laser generator 2, lenses 5, 6 and other components disposed outside the cutting zone 8 from debris and dirt received in the cutting zone 8. However, it will be understood that the windows 9a, 9b may be omitted.

The cutting zone 8 comprises a middle section 8a, a first outer section 8b and a second outer section 8c. The first outer section 8b is defined between one end of the cutting zone 8 and the middle section 8a. The second outer section 8c is defined between the other end of the cutting zone 8 and the middle section 8a.

The laser beam 4 travels through the cutting zone 8 along an optical axis 10 of the beam 4. Gaussian theory dictates that laser beams have a natural intensity variation along their length. Beams will have a focal point where the laser beam has maximum intensity (power per unit area) and minimum width, meaning the focal point is the most effective part of the laser beam for severing hair by optical absorption. On the other hand, parts of the laser beam furthest from the focal point will have a larger width and therefore a more distributed intensity and will not be as effective at severing hair because the energy of the laser beam is incident over a larger area of hair. Therefore, there is a variation in hair severing performance along the optical axis of a laser beam. Due to the natural divergence of Gaussian laser beams it is impossible to achieve a uniform beam thickness along an optical axis.

The laser beam 4 in the cutting zone 8 will conform to Gaussian theory and will comprise a 'first focal point' 11, or waist, located along an optical axis 10 of the beam 4. The focal point 11 is the position of maximum intensity and minimum width and the most effective part of the beam 4 for severing hair because the laser beam energy is concentrated on a smaller area of the hair to be severed, increasing the rate of optical absorption. Regions 12, 13 either side of the waist 11 have a larger beam width and lower intensity so are less effective for severing hair because the laser beam energy is distributed over a larger area of the hair. This arrangement may lead to a slight variation in cutting performance across the cutting zone 8 as the first focal point 11 of the laser beam 4 severs hairs more cleanly and at a different length to the other regions 12, 13 either side of the waist 11. However, it will be understood that the intensity of the beam in the regions 12, 13 either side of the waist 11 will be sufficient to sever hair received in the cutting zone 8.

Gaussian beam theory can be used to determine the natural variation in intensity along a beam by considering the change in beam width (cross-sectional area) caused by divergence. The divergence of a perfect Gaussian laser beam is defined by the following equation:

$$w(z) = w_0 \sqrt{1 + M^2 \left(\frac{z^2}{z_R^2}\right)}$$

Wherein:
w(z) is the beam radius at a distance z from the beam waist (focal point),
$w_0$ is the radius of the beam waist, and
$z_R$ is the Rayleigh range,
while $M^2$ is the beam propagation factor which is a measure of beam quality.

The Rayleigh range ($z_R$) of a laser beam is defined as the distance over which the beam surface area is doubled and is described by the following equation:

$$z_R = \frac{\pi \cdot w_0^2}{\lambda}$$

Wherein $\lambda$ is the wavelength of the laser beam.

The Rayleigh range is the portion of the beam with the highest intensity, making it the most effective part of the beam for cutting hair because the energy of the laser beam is focused on a smaller area of the hair. The Rayleigh range, or high intensity region, is represented by the dotted line 14 in FIG. 1 which is in a fixed position. Regions 12, 13 of the beam outside of the Rayleigh range 14 have a larger beam width with a less concentrated energy distribution. Therefore, the hair cutting characteristics of these regions will not be as effective at cutting hair as in the Rayleigh range 14. A well designed laser shaver should not generate a laser beam that is significantly more powerful than required to sever hairs because of power requirements, excessive heat and skin irritation. Therefore, it is important to utilise the high intensity region 14 effectively in a laser shaver, together with the regions 12, 13 immediately on each side of the high intensity region 14.

It will be understood that the high intensity region 14, together with the regions 12, 13 immediately on each side of the high intensity region 14, define an effective cutting area. That is, the section of the laser beam 4 which has effective cutting characteristics to cut hair.

Figure 2:
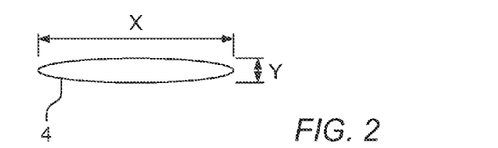
FIG. 2 shows a cross-sectional view of a laser beam along the optical axis of the laser beam.

The laser beam 4 emitted by the laser generator 2 is elliptical in cross-section. A cross-sectional view of the laser beam 4 in focus is shown in FIG. 2. The laser beam has a dimension Y along the y-axis and a dimension X along the x-axis. It will be understood that the optical axis 10 of the laser beam 4 extends along the z-axis (refer to FIG. 1), wherein the x, y and z axes are perpendicular to each other.

The laser beam 4 is emitted from a laser stripe (not shown) of the laser generator 2. The laser stripe (not shown) extends parallel to the x-axis. The arrangement of a laser generator is known and so a detailed description will be omitted herein. The divergence of the laser beam 4 is different in the direction parallel and perpendicular to the laser stripe, also known as the near field.

The divergence of the beam in the y-axis is called the fast axis. In the present arrangement, the fast axis has a beam divergence of about 40° (full angle, $1/e^2$). The divergence of the beam in the x-axis is called the slow axis. In the present arrangement, the slow axis has a beam divergence of about 10°. That is, the angle of divergence of the laser beam along the y-axis is greater than the angle of divergence of the laser beam 4 in the x-axis. The dimension of the near field along the y-axis is about 2 µm. The dimension of the near field along the x-axis is about 20 µm.

The focus lens 6 causes the laser beam 4 to converge along the fast axis (y-axis) and the slow axis (x-axis) as the beam extends along its optical axis 10. The focus lens 6 defines the first focal length of the laser beam 4. The first focal length of the laser beam 4 is the distance between the focus lens 4 and the first focal point 11 of the laser beam 4. In the present embodiment the focus lens is configured to cause the first focal length of the laser beam 4 along its fast and slow axes to be the same.

A focusing element 15 is disposed in the cutting zone 8. The focusing element 15 is incident with the optical axis 10 of the laser beam 4. The focusing element 15 is configured to refocus the laser beam 4 passing through the cutting zone 8. That is, the focusing element is configured to form a second focal point 16 of the laser beam 4 along its optical axis 11.

The focusing element 15 is disposed in the middle section 8a of the cutting zone 8. Therefore, the first outer section 8b of the cutting zone 8 is defined on one side of the focusing element 15, and the second outer section 8c of the cutting zone 8 is defined on the other side of the focusing element 15.

The focusing element 15 is a spherical lens. That is, the focusing element 15 is configured to focus the laser beam in both of its fast axis and slow axis. In the present embodiment, the focal length of the focusing element 15 is substantially equal to the focal length of the focus lens 6.

The focusing element 15 is a refractive lens. That is, the laser beam 4, which is incident on the focusing element 15, passes through the focusing element 15 and is focused by refraction as it passes through the focusing element 15.

The distance between the focus lens 6 and the focusing element 15 along the optical axis 10 of the laser beam 4 is greater than the first focal length of the laser beam 4. Therefore, the laser beam 4 diverges between the first focal point 11 and the focusing element 15.

The length of the first outer section 8b of the cutting zone 8 is about double the first focal length of the laser beam 4. The length of the second outer section 8c of the cutting zone 8 is about double the second focal length of the laser beam 4.

The cutting head 1 further comprises a body 17 with a spacer 18 that contacts a section of the skin 19 of a user to maintain protective separation between the laser beam 4 and the skin 19. The spacer 18 comprises a cutting surface against which a user's skin 19 is locatable. The spacer 18 comprises at least one opening (not shown). The spacer 18 allows hairs (not shown) to protrude into the cutting zone 8. The cutting zone 8 is defined in the region above the spacer 18. The spacer 18 comprises a single, elongate opening (not shown) that is parallel to the optical axis 10 of the laser beam 4 through which hairs are received for cutting. Alternatively, the spacer 18 may have an alternative arrangement, such as a plurality of circular, hexagonal or similar openings (not shown) through which the hair is received into the cutting zone 8. Alternatively, the spacer 18 may comprise a comb with a plurality of teeth that manipulate the hairs into the cutting zone 8.

When the laser generator 2 is operated, the emitted laser beam 4 is directed towards the optical system 3. The laser beam 4 is focused by the focus lens 6 to cause the beam 4 to converge. The laser beam 4 travels through the first outer section 8b of the cutting zone 8, along the optical axis 10 of the beam 4.

The first focal point 11 of the laser beam 4 is in the first outer section 8b. As the distance between the focus lens 6 and the focusing element 15 is greater than the first focal length of the laser beam 4 caused by the focus lens 6, the first focal point 11 of the laser beam 4 is formed in the first outer section 8b. A first effective cutting area of the laser beam 4 is therefore formed in the first outer section 8b. The section of the laser beam 4 in the first outer section 8b is a first cutting section 20 of the laser beam.

It will be understood that the laser beam 4 diverges between the first focal point 11 and the focusing element 15. The focusing element 15 is disposed on the optical axis 10 of the laser beam 10 and so the laser beam 4 is directed towards the focusing element 15. The laser beam 4 is focused by the focusing element 15. The laser beam 4 is refocused by the focusing element 15 along the fast axis (y-axis) and the slow axis (x-axis).

The second focal point 16 of the laser beam 4 is in the second outer section 8c. That is, the second focal point 16 of the laser beam 4 is formed in the cutting zone 8. The distance between the focusing element 15 and the end of the cutting zone 8, which in the present embodiment is formed by the second window 9b, is greater than the second focal length of the laser beam 4 caused by the focusing element 15. The second effective cutting area of the laser beam 4 is formed in the second outer section 8c. The section of the laser beam 4 in the second outer section 8c is a second cutting section 21 of the laser beam.

The focusing element 15 causes another Rayleigh range. The Rayleigh range, or high intensity region, of the second cutting section 21 of the laser beam 4 is represented by the dotted line 22 in FIG. 1. Regions 23, 24 of the beam outside of the Rayleigh range 22 have a larger beam width with a less concentrated energy distribution. It will be understood that the high intensity region 22 of the second cutting section 21, together with the regions 23, 24 immediately on each side of the high intensity region 22, define an effective cutting area. That is, another section of the laser beam 4 which has effective cutting characteristics to cut hair.

With the above arrangement, the cutting head 1 is provided with two effective cutting areas in the cutting zone 8. Therefore, the length of the cutting zone 8 can be doubled and the laser beam is capable of effectively cutting a hair substantially along the length of the cutting zone 8. A minimal non-effective cutting area will be formed in the cutting zone 8 at the position of the focusing element 15, however it will be understood that this non-effective region is minimal in comparison the extended length of the cutting zone 8 that is provided by the above described arrangement. Furthermore, the cutting head 1 will generally be passed two or more times over a portion of skin to ensure complete removal of hair therefrom.

The diameter of a hair is generally about 100 μm. In the present arrangement, the dimension of the laser beam 4 along the x-axis at the first focal point 11 is about 250 μm ($1/e^2$). The dimension of the laser beam 4 along the y-axis at the first focal point 11 is about 25 μm ($1/e^2$). As the distance between the focus lens 6 and the focusing element 15 is about double the first focal length of the laser beam 4, and the second focal length of the laser beam 4 is about the same as the first focal length, then the dimension of the laser beam 4 along the x-axis at the second focal point 16 is about 250 μm ($1/e^2$). The dimension of the laser beam 4 along the y-axis at the second focal point 16 is about 25 μm ($1/e^2$).

An advantage of the above arrangement is that a large treatment stroke of the laser beam 4 in the cutting zone 8 having a power density sufficient to effectively cut hair received in the cutting zone 8 is provided, whilst minimising the necessary power of the head laser generator 2. Therefore, the efficiency of the head unit 1 is maximised.

When hairs are received in the cutting zone 8 they are exposed to the first or second cutting sections 20, 21 of the laser beam 4 in the cutting zone 8. Therefore, the hairs are cut by laser ablation.

The laser beam 4 subsequently passes from the cutting zone 8 and travels away from the cutting zone 8. The exit section of the beam 4 may then be absorbed within the energy dissipater or similar device (not shown) to prevent damage being caused by the energy of the remaining laser beam 4.

In the above arrangement the focusing element is spherical. That is, the first focusing element is configured to focus the laser beam 4 in both of the fast axis and the slow axis. However, in an alternative arrangement the focusing element is cylindrical. That is, the focusing element is configured to focus the laser beam in one of the fast axis or the slow axis only.

Figure 3:
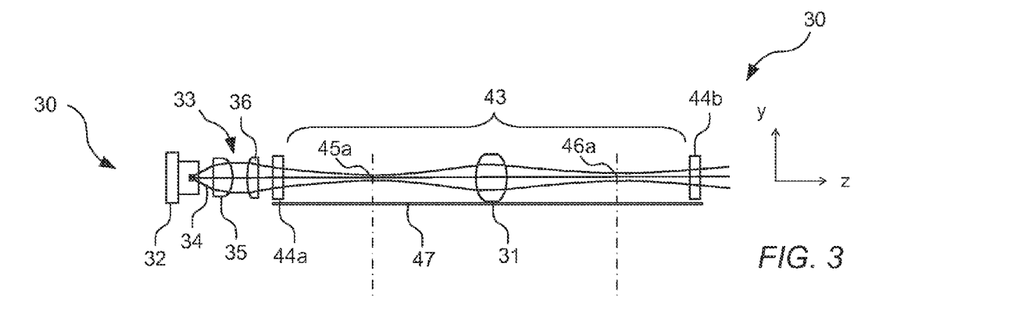
FIG. 3 shows a schematic side view of a cutting head of another embodiment of a device for cutting hair.
Figure 4:
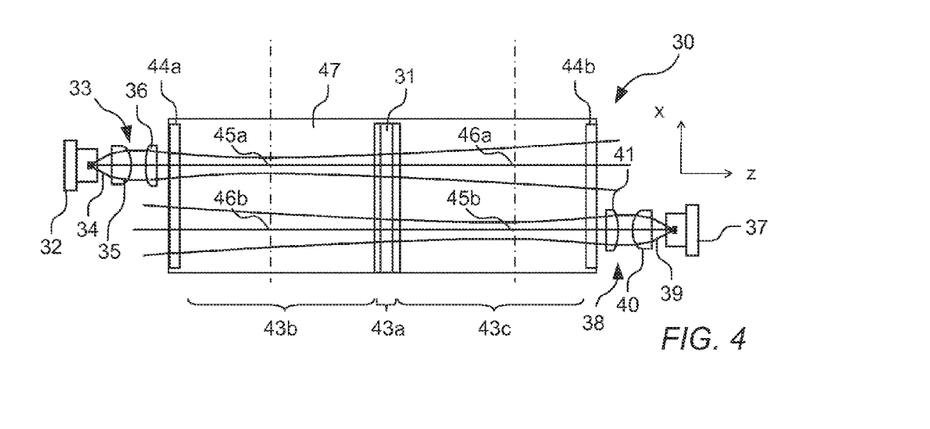
FIG. 4 shows a schematic plan view of the cutting head shown in FIG. 3.

FIGS. 3 and 4 show an exemplary embodiment of a cutting head 30 for cutting hair having a focusing element 31 that is cylindrical. The arrangement of the cutting head shown in FIGS. 3 and 4 is generally the same as that of the cutting head 1 described above and so a detailed description is omitted herein. A number of the features and components correspond to features and components described above, and so a detailed description will be omitted. However, instead of the spherical focusing element 15, as described with reference to FIG. 1, the optical system of FIG. 3 comprises the cylindrical focusing element 31.

Referring now to FIGS. 3 and 4, the head unit 30 comprises a first laser generator 32, acting as a laser source, and a first optical system 23. The first laser generator 32 emits a first laser beam 34. The first laser beam 34 follows an optical path in the head unit 30 from the first laser generator 32 along a first optical axis. It will be understood that the optical axis extends along the z-axis as shown in the Figures, and that the cutting head is configured to be moved over a user's skin in a direction along the x-axis in order to cut hairs.

The emitted laser beam 34 is directed towards the first optical system 33. The first optical system 33 has a first collimating lens 35 and a first focus lens 36. The first laser beam 34 is directed towards the first collimating lens 35. The first collimating lens 35 reduces or eliminates the divergence of the beam. The first laser beam 34 is then focused by the first focus lens 36 to cause the beam 34 to converge.

The head unit 30 also comprises a second laser generator 37, acting as a laser source, and a second optical system 38. The second laser generator 37 emits a second laser beam 39. The second laser beam 39 follows an optical path in the head unit 30 from the second laser generator 37 along a second optical axis. In the present embodiment, the first and second optical axes extend parallel to, but offset from, each other.

The emitted second laser beam 39 is directed towards the second optical system 38. The second optical system 38 has a second collimating lens 40 and a second focus lens 41. The second laser beam 39 is directed towards the second collimating lens 40. The second collimating lens 40 reduces or eliminates the divergence of the beam. The second laser beam 39 is then focused by the second focus lens 41 to cause the beam 39 to converge.

In the present arrangement, the emitted laser beams are multi-transverse-mode blue diode lasers. The wavelength of the emitted laser beams are about 450 nm. The power of the emitted laser beams is in the order of magnitude of 3 W. However, it will be understood that characteristics of the laser beams may be varied.

The head unit 30 has a cutting zone 43 in which hairs are received to be cut. The first and second laser generators 32, 37 are disposed on opposite sides of the cutting zone 43. A first window 44a is disposed between the cutting zone 43 and the first focus lens 36. A second window 44b is disposed at the other end of the cutting zone 43 to the first window 44a. The second window 44b is disposed between the cutting zone 43 and the second focus lens 41. Energy dissipaters or similar devices (not shown) are disposed behind the first and second windows 44a, 44b to dissipate the energy of the remaining laser beams 34, 39. However, it will be understood that the windows 44a, 44b may be omitted.

Each laser beam 34, 39 in the cutting zone 43 will conform to Gaussian theory and will comprise a 'first focal point' 45a, 45b, or waist, located along its optical axis. The high intensity regions at the first focal points 45a, 45b, together with the regions immediately on each side of the high intensity regions, define effective cutting areas. That is, the section of each laser beam 34, 39 which has effective cutting characteristics to cut hair.

The focus lenses 36, 41 cause the respective laser beams 34, 39 to converge along the fast axis (y-axis) and the slow axis (x-axis) as the beams extend along their optical axes. The focus lenses 36, 41 define the first focal length of each laser beam. In the present embodiment the focus lenses 36, 41 are configured to cause the first focal length of the laser beams 34, 39 along both their fast and slow axes to be the same. However, it will be understood that the focal length of the fast axis of each laser beam may differ from the focal length of the slow axis, as will become apparent below.

The focusing element 31 is disposed in the cutting zone 43. The focusing element 31 acts as a focusing element 31 for both the first and second laser beams 34, 39. That is, the focusing element 31 forms part of the first and second optical systems 33, 38. The focusing element 31 is incident with the optical axis of the first laser beam 34. The focusing element 31 is configured to refocus the first laser beam 34 passing through the cutting zone 43. That is, the focusing element 31 is configured to form a second focal point 46a of the first laser beam 34 along its optical axis.

The focusing element 31 is incident with the optical axis of the second laser beam 39. The focusing element 31 is configured to refocus the second laser beam 39 passing through the cutting zone 43. That is, the focusing element 31 is configured to form a second focal point 46b of the second laser beam 39 along its optical axis.

The focusing element 31 is a refractive lens. The focusing element 31 is a cylindrical lens. That is, the focusing element 31 is configured to focus a laser beam in one of the fast axis or the slow axis only.

In the present embodiment, the focusing element 31 is configured to focus each of the laser beams 34, 39 along its fast axis. The fast axis extends along the x-axis. Therefore, the second focal point 46a, 46b is the focal point of the fast axis of each laser beam 34, 39 only. The slow axis of each laser beam 34, 39 is not refocused by the focusing element 31. The cylindrical surfaces of the focusing element 31 may be toriodal shaped surfaces.

In the present embodiment, the focal length of the focusing element 31 is substantially equal to the focal length of each of the focus lenses 36, 41. The second focal point 46b of the second laser beam 39 aligns with the first focal point 45a of the first laser beam 34. Similarly, the first focal point 46a of the second laser beam 39 aligns with the second focal point 46a of the first laser beam 34. However, it will be understood that the focal points of the first and second laser beams 34, 39 may be offset from each other.

The cutting head 30 further comprises a body with a spacer 47 that contacts a section of the skin of a user to maintain protective separation between the laser beams 34, 39 and the skin.

When the laser generators 32, 37 are operated, the emitted laser beams 34, 39 are focused by the first and second focus lenses 36, 41 respectively. The focusing element 31 is disposed in a middle section 43a of the cutting zone 43. The first laser beam 34 travels through a first outer section 43b of the cutting zone 43 and the second laser beam 39 travels through the second outer section 43c of the cutting zone 43.

The first focal point 45a of the first laser beam 34 is in the first outer section 43b. A first effective cutting area of the first laser beam 34 is therefore formed in the first outer section 43b. The first focal point 45a is a focal point in the fast and slow axes of the beam.

The first laser beam 34 diverges between the first focal point 45a and the focusing element 31. The first laser beam 34 is then re-focused by the focusing element 31. The first laser beam 34 is refocused by the focusing element 31 along the fast axis (y-axis) only. The focusing element 31 is a cylindrical lens and so does not focus the first laser beam 34 along its slow axis (x-axis), which continues to diverge. The second focal point 46a of the first laser beam 34 is formed in the second outer section 43c. A second effective cutting area of the first laser beam 34 is formed in the second outer section 43c.

Figure 5:
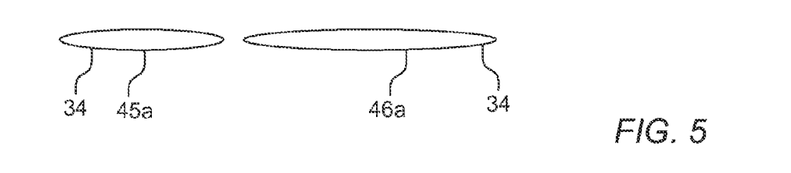
FIG. 5 shows a cross-sectional view of a laser beam of the embodiment of a device for cutting hair shown in FIGS. 3 and 4 along the optical axis of the laser beam at first and second focal points.

A cross-sectional view of the first laser beam 34 at the first and second focal points 45a, 46a is shown in FIG. 5. The first laser beam 34 has corresponding dimensions along the y-axis at the first and second focal points 45a, 46a because the laser beam is refocused by the focusing element along its fast axis. However, the dimension X at the second focal point 46a is greater than the dimension X at the first focal point 45a because the laser beam is not refocused along its slow axis. The second focal point 46a, and the second effective cutting area, of the first laser beam 34 will have a slightly lower peak power due to the beam not being refocused in by the focusing element 31, but will cause a larger exposure time of a hair as the laser beam is moved across a hair with due to the increase in the X dimension of the beam.

The first focal point 45b of the second laser beam 39 is in the second outer section 43c. A first effective cutting area of the second laser beam 39 is therefore formed in the second outer section 43c. The second focal point 45b is a focal point in the fast and slow axes of the beam.

The second laser beam 39 diverges between the first focal point 45b and the focusing element 31. The second laser beam 39 is then re-focused by the focusing element 31. The second laser beam 39 is refocused by the focusing element 31 along the fast axis (y-axis) only. The second focal point 46b of the first laser beam 34 is formed in the second outer section 43c. A second effective cutting area of the first laser beam 34 is formed in the first outer section 43b.

The second focal point 46b, and the second effective cutting area, of the second laser beam 39 will have a slightly lower peak power due to the beam not being refocused in by the focusing element 31, but will cause a larger exposure time of a hair as the laser beam is moved across a hair with due to the increase in the X dimension of the beam.

With the above arrangement, the cutting head 30 is provided with multiple effective cutting areas in the cutting zone 43. Therefore, the length of the cutting zone 43 is increased and the laser beams are capable of effectively cutting a hair substantially along the length of the cutting zone 43.

The laser beams 34, 39 subsequently pass from the cutting zone 43 and travel away from the cutting zone 43. The exit section of the beams may then be absorbed within the energy dissipaters or similar devices (not shown) to prevent damage being caused by the energy of the remaining laser beam 34, 39.

Furthermore, it is possible to use a single cylindrical lens acting as a focusing element to refocus two or more laser beams. This simplifies ease and cost of manufacture of the cutting head. In the present arrangement, the focusing element 31 is extended to refocus two laser beams. An advantage of using such a cylindrical focusing element 31 is that it is easier to manufacture than an extended spherical lens.

In the above arrangement the cutting head has two laser generators. This arrangement maximizes the efficiency of the cutting head and helps to ensure that the cutting head provides a generally symmetrical cutting action along its length. However, it will be understood that in an alternative arrangement a cutting head is used with a cylindrical lens and a single laser generator only to form a single laser beam in the cutting head (not shown). Furthermore, it will be understood that in an alternative arrangement three or more laser beams may be used.

Figure 6:
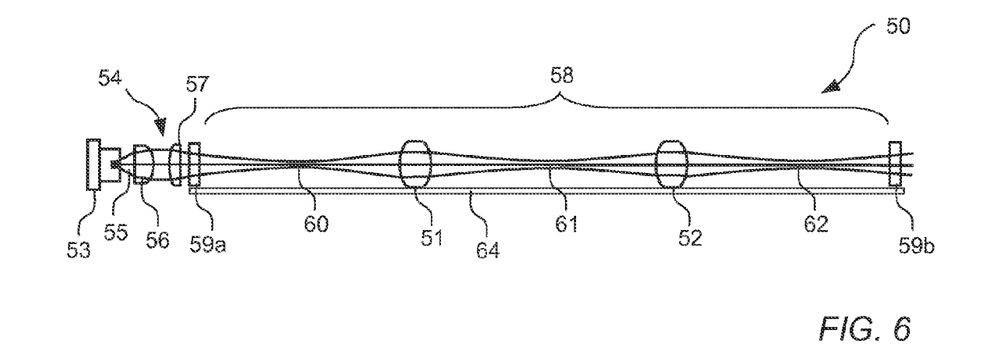
FIG. 6 shows a schematic side view of a cutting head of another embodiment of a device for cutting hair.

FIG. 6 shows another embodiment of a cutting head 50 for cutting hair. The arrangement of the cutting head 50 shown in FIG. 6 is generally the same as that of the cutting heads described above and so a detailed description is omitted herein. A number of the features and components correspond to features and components described above, and so a detailed description will be omitted. In this arrangement, the cutting head 50 comprises first and second focusing elements 51, 52.

The head unit 50 comprises a laser generator 53, acting as a laser source, and an optical system 54. The laser generator 53 emits a laser beam 55. The laser beam 55 follows an optical path in the head unit 50 from the laser generator 53 along an optical axis. The emitted laser beam 55 is directed towards the optical system 54. The optical system 54 has a collimating lens 56 and a focus lens 57. The laser beam 55 is directed towards the collimating lens 56 and is then focused by the focus lens 57 to cause the beam 55 to converge.

The head unit 50 has a cutting zone 58 in which hairs are received to be cut. A first window 59a is disposed between the cutting zone 58 and the focus lens 57. A second window 59b is disposed at the other end of the cutting zone 58 to the first window 59a. However, it will be understood that the windows 59a, 59b may be omitted.

The laser beam 55 in the cutting zone 58 will conform to Gaussian theory and will comprise a 'first focal point' 60, or waist, located along its optical axis. The high intensity regions at the first focal point 60, together with the regions immediately on each side of the high intensity regions, define an effective cutting area. That is, the section of the laser beam 55 which has effective cutting characteristics to cut hair.

The focus lens 57 cause the laser beam 55 to converge along the fast axis (y-axis) and the slow axis (x-axis) as the beams extend along their optical axes. The focus lens 57 defines the first focal length of the laser beam. In the present embodiment the focus lens 57 is configured to cause the first focal length of the laser beam 55 along both its fast and slow axes to be the same. However, it will be understood that the focal length of the fast axis may differ from the focal length of the slow axis, as will become apparent below.

The first and second focusing elements 51, 52 are disposed in the cutting zone 58. The first focusing element 51 is incident with the optical axis of the laser beam 55. The second focusing element 52 is incident with the optical axis of the laser beam 55. The first and second focusing elements 51, 52 are spaced apart from each other.

The first and second focusing elements 51, 52 are configured to refocus the laser beam 55 passing through the cutting zone 58. That is, the first focusing element 51 is configured to form a second focal point 61 of the laser beam 55 along its optical axis. Similarly, the second focusing element 52 is configured to form a third focal point 62 of the laser beam 55 along its optical axis.

The focusing elements 51, 52 are refractive lenses. The focusing elements 51, 52 are cylindrical lens. That is, the focusing elements 51, 52 are configured to focus a laser beam in both of the fast axis and the slow axis.

The cutting head 50 further comprises a body with a spacer 64 that contacts a section of the skin of a user to maintain protective separation between the laser beam and the skin.

In the present embodiment, the focal length of the first and second focusing elements 51, 52 are substantially equal to the focal length of the focus lens 57. However, it will be understood that the focal lengths of the first and second focusing elements 51, 52 may differ from the focus lens 57 and each other.

When the laser generator 53 are operated, the emitted laser beam 55 is focused by the focus lens 57. The first focal point 60 of the laser beam 55 is formed in the cutting zone 58 between the focus lens 57 and the first focusing element 51. A first effective cutting area of the laser beam 55 is therefore formed in the cutting zone 58.

The laser beam 55 diverges between the first focal point 60 and the first focusing element 51. The laser beam 55 is then re-focused by the first focusing element 51. The laser beam 55 is refocused by the first focusing element 51 along its fast and slow axes. The second focal point 61 of the laser beam 55 is formed between the first and second focusing elements 52. A second effective cutting area of the laser beam 55 is therefore formed in the cutting zone 58.

The laser beam 55 diverges again between the second focal point 61 and the second focusing element 52. The laser beam 55 is then re-focused by the second focusing element 52. The laser beam 55 is refocused by the second focusing element 52 along its fast and slow axes. The third focal point 62 of the laser beam 55 is formed between the second focusing element 52 and the distal end of the cutting zone 58. A third effective cutting area of the laser beam 55 is therefore formed in the cutting zone 58.

With the above arrangement, the cutting head 30 is provided with three effective cutting areas in the cutting zone 43. Therefore, the length of the cutting zone 58 is increased and the laser beam is capable of effectively cutting a hair along the length of the cutting zone 58.

The laser beam 55 subsequently passes from the cutting zone 58 and travel away from the cutting zone 58. The exit section of the beam may then be absorbed within the energy dissipater or similar device (not shown) to prevent damage being caused by the energy of the remaining laser beam 55.

In the above arrangement the first and second focusing elements are spherical. That is, each of the first and second focusing elements are configured to focus the laser beam in both of the fast axis or the slow axis. However, it will be understood that in an alternative arrangement one or both of the first and second focusing elements may be cylindrical lenses. That is, each or one of the first and second focusing elements are configured to focus the laser beam in one of the fast axis and the slow axis only.

With such an arrangement, the head unit 50 may be configured to have two or more laser beams (not shown) passing through the cutting zone. In an exemplary arrangement with two or more laser beams, the laser beams are configured to be aligned and disposed in a similar arrangement to the arrangement shown in FIGS. 3 and 4. However, in this exemplary arrangement each laser beam has an optical axis which is incident with two or more focusing elements.

In the above described embodiments, the focusing element or elements are refractive lenses. That is, a laser beam, which is incident on the focusing element, is focused by refraction as it passes through the focusing element. However, in another embodiment the focusing element is a reflective lens. That is, a laser beam, which is incident on the focusing element, is focused as it is reflected by the focusing element. One such embodiment in which the focusing element is a reflective lens is shown in FIG. 7.

Figure 7:
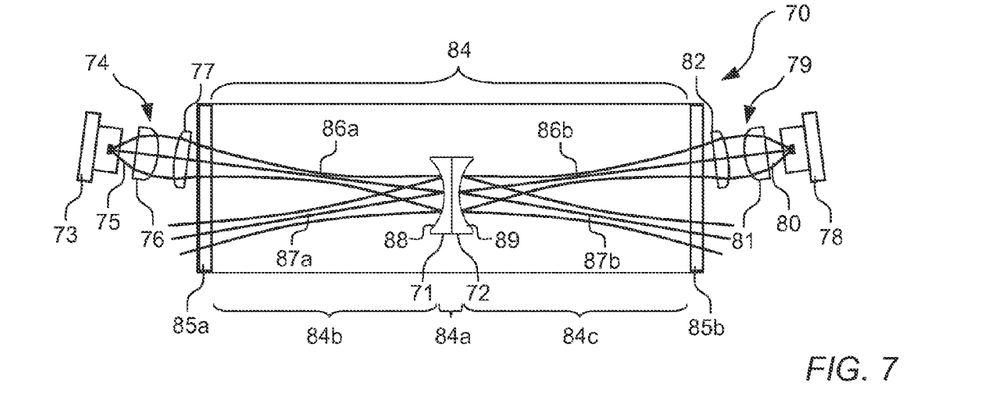
FIG. 7 shows a schematic plan view of a cutting head of another embodiment of a device for cutting hair.

FIG. 7 shows an exemplary embodiment of a cutting head 70 for cutting hair having a focusing element that is a reflective lens. The arrangement of the cutting head shown in FIG. 7 is generally the same as that of the cutting heads described above and so a detailed description is omitted herein. A number of the features and components correspond to features and components described above, and so a detailed description will be omitted. However, instead of the reflective lenses, as described with reference to FIGS. 1 to 6, the optical system of FIG. 7 comprises first and second reflective lenses 71, 72 acting as focusing elements.

Referring now to FIG. 7, the head unit 70 comprises a first laser generator 73, acting as a laser source to emit a first laser beam 75, and a first optical system 74. The first laser beam 75 follows an optical path in the head unit 70 from the first laser generator 73 along a first optical axis. The emitted laser beam 75 is directed towards the first optical system 74. The first optical system 74 has a first collimating lens 76 and a first focus lens 77. The first laser beam 75 is directed towards the first collimating lens 76 and is then focused by the first focus lens 77 to cause the beam 75 to converge.

The head unit 70 also comprises a second laser generator 78, acting as a laser source to emit a second laser beam 80, and a second optical system 79. The second laser beam 80 follows an optical path in the head unit 70 from the second laser generator 78 along a second optical axis. The emitted second laser beam 80 is directed towards the second optical system 79. The second optical system 79 has a second collimating lens 81 and a second focus lens 82. The second laser beam 80 is directed towards the second collimating lens 81 and is then focused by the second focus lens 82 to cause the beam 80 to converge.

The head unit 30 has a cutting zone 84 in which hairs are received to be cut. The first and second laser generators 73, 78 are disposed on opposite sides of the cutting zone 84. A first window 85a is disposed between the cutting zone 84 and the first focus lens 77. A second window 85b is disposed at the other end of the cutting zone 84 to the first window 85a. The second window 85b is disposed between the cutting zone 84 and the second focus lens 82. Energy dissipaters or similar devices (not shown) are disposed behind the first and second windows 85a, 85b to dissipate the energy of the remaining laser beams 75, 80. However, it will be understood that the windows 85a, 85b may be omitted.

Each laser beam 75, 80 in the cutting zone 84 will conform to Gaussian theory and will comprise a 'first focal point' 86a, 86b, or waist, located along its optical axis. The high intensity regions at the first focal points 86a, 86b, together with the regions immediately on each side of the high intensity regions, define effective cutting areas. That is, the section of each laser beam 75, 80 which has effective cutting characteristics to cut hair.

The focus lenses 77, 82 define the first focal length of each laser beam. In the present embodiment the focus lenses 77, 82 are configured to cause the first focal length of the laser beams 75, 80 along both their fast and slow axes to be the same. However, it will be understood that the focal length of the fast axis of each laser beam may differ from the focal length of the slow axis, as will become apparent below.

The first and second focusing elements 71, 72 are disposed in the cutting zone 84. The first and second focusing elements 71, 72 oppose each other. The first focusing element 71 has a first focusing surface 88, and the second focusing element 72 has a second focusing surface 89. The first and second focusing surfaces 88, 89 face away from each other. It will be understood that the first and second focusing elements 71, 72 may be integrally formed.

The first focusing element 71 acts as a focusing element for the first laser beam 75. The first focusing element 71 is incident with the optical axis of the first laser beam 75. The first focusing element 71 is configured to refocus the first laser beam 75 passing through the cutting zone 84. That is, the first focusing element 71 is configured to form a second focal point 87a of the first laser beam 75 along its optical axis.

The second focusing element 72 acts as a focusing element for the second laser beam 80. The second focusing element 72 is incident with the optical axis of the second laser beam 80. The second focusing element 72 is configured to refocus the second laser beam 80 passing through the cutting zone 84. That is, the second focusing element 72 is configured to form a second focal point 87b of the second laser beam 80 along its optical axis.

The focusing elements 71, 72 are reflective lenses. The focusing surfaces 88, 89 are reflective. The focusing surfaces 88, 89 are concave to focus the respective laser beam incident on them. In the present embodiment, the focusing elements are each a spherical lens. That is, the focusing elements are configured to focus a laser beam along both of the fast axis and the slow axis.

In the present embodiment, the focal length of the first and second focusing elements 71, 72 are substantially equal to the focal length of the focus lenses 77, 82. However, it will be understood that the focal lengths of the first and second focusing elements 71, 72 may differ from the focus lenses and each other.

When the laser generators 73, 78 are operated, the emitted laser beams 75, 80 are focused by the first and second focus lenses 77, 82 respectively. The first and second focusing elements 71, 72 are disposed in a middle section 84a of the cutting zone 84. The first laser beam 75 travels through a first outer section 84b of the cutting zone 84 and the second laser beam 80 travels through the second outer section 84c of the cutting zone 80.

The first focal point 86a of the first laser beam 75 is in the first outer section 84b. The first focal point 86a of the first laser beam 75 is formed between the first focus lens 77 and the first focusing element 71. A first effective cutting area of the first laser beam 75 is therefore formed in the first outer section 84b.

The first laser beam 75 diverges between the first focal point 86a and the first focusing element 71. The first laser beam 75 is then re-focused by the first focusing element 71. The first laser beam 75 is reflected back into the first outer section 84b. The laser generator 73 is configured to form the optical path of the first laser beam 75 at an angle to the reflective surface 88 of the first focusing element 71. Therefore, a second portion of the optical path of the first laser beam 75 in the cutting zone 84 extends at an angle to a first portion. That is, the path of the reflected part of the laser beam diverges away from the initial path of the beam. The second focal point 87a of the first laser beam 75 is formed in the first outer section 84b. A second effective cutting area of the first laser beam 75 is formed in the first outer section 84b. Therefore, two effective cutting areas are formed by the first laser beam 75.

The first focal point 86b of the second laser beam 80 is in the second outer section 84c. The first focal point 86b of the second laser beam 80 is formed between the second focus lens 82 and the second focusing element 89. A first effective cutting area of the second laser beam 80 is therefore formed in the second outer section 84c.

The second laser beam 80 diverges between the first focal point 86b and the second focusing element 72. The second laser beam 80 is then re-focused by the second focusing element 72. The second laser beam 80 is reflected back into the second outer section 84c. The second laser generator 78 is configured to form the optical path of the second laser beam 80 at an angle to the reflective surface 89 of the second focusing element 72. Therefore, a second portion of the optical path of the second laser beam 80 in the cutting zone 84 extends at an angle to a first portion. That is, the path of the reflected part of the laser beam diverges away from the initial path of the beam. The second focal point 87b of the second laser beam 80 is formed in the second outer section 84c. A second effective cutting area of the second laser beam 80 is formed in the second outer section 84c. Therefore, two effective cutting areas are formed by the second laser beam 80.

With the above arrangement, the cutting head 70 is provided with multiple effective cutting areas in the cutting zone 84. Therefore, the length of the cutting zone 84 is increased and the laser beams are capable of effectively cutting a hair substantially along the length of the cutting zone 84. Therefore, the effectiveness and efficiency of the cutting head 70 is maximised.

The laser beams 75, 80 subsequently pass from the cutting zone 84 and travel away from the cutting zone 84. The exit section of the beams may then be absorbed within the energy dissipaters or similar devices (not shown) to prevent damage being caused by the energy of the remaining laser beam 75, 80.

Although in the above embodiment described with reference to FIG. 7 the optical system comprises two reflective lenses, it will be understood that in an alternative embodiment the optical system comprises one reflective lens, or three or more reflective lenses. In an exemplary embodiment having one reflective lens (not shown), the reflective lens acting as the focusing element is disposed at one end of the cutting zone. That is, the reflective lens is disposed at the distal end of the cutting zone to the laser generator to refocus and reflect the laser beam back across the cutting zone.

In the above arrangement the first and second focusing elements are spherical. That is, each of the first and second focusing elements 71, 72 are configured to focus the laser beams 75, 80 in both of their fast axis and the slow axis. However, it will be understood that in an alternative arrangement one or both of the first and second focusing elements may be a cylindrical lens. That is, the or each of the focusing elements is configured to focus the laser beam in one of the fast axis and the slow axis only. It will also be understood that one or more refractive lenses, acting as further focusing elements, may be used together with the or each of the reflective elements, acting as focusing elements.

Figure 8:
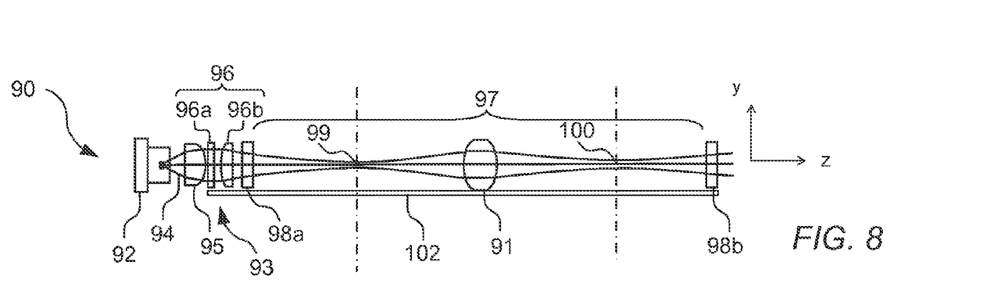
FIG. 8 shows a schematic side view of a cutting head of another embodiment of a device for cutting hair.
Figure 9:
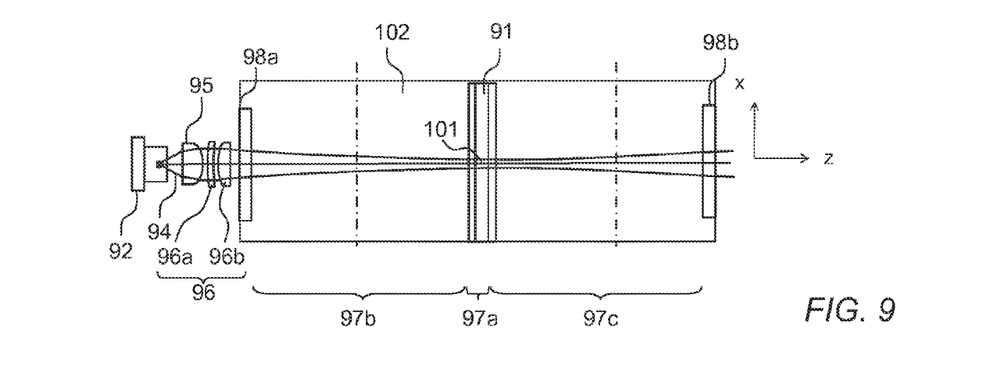
FIG. 9 shows a schematic plan view of the cutting head shown in FIG. 8.

FIGS. 8 and 9 show another embodiment of a cutting head 90 for cutting hair. The arrangement of the cutting head shown in FIGS. 8 and 9 is generally the same as that of the cutting heads described above and so a detailed description is omitted herein. A number of the features and components correspond to features and components described above, and so a detailed description will be omitted. In this arrangement, the focal point of the slow axis is offset from at least one of the focal points of the fast axis.

Referring now to FIGS. 8 and 9, the head unit 90 comprises a laser generator 92, acting as a laser source, and an optical system 93. The laser generator 92 emits a laser beam 94. The laser beam 94 follows an optical path in the head unit 90 from the laser generator 92 along an optical axis.

The emitted laser beam 94 is directed towards the optical system 93. The optical system 93 has a collimating lens 95 and a focus lens 96. The laser beam 94 is directed towards the collimating lens 95. The collimating lens 95 reduces or eliminates the divergence of the beam. The laser beam 94 is then focused by the focus lens 96 to cause the beam 94 to converge.

The focus lens 96 is configured to focus the laser beam 94 along both its fast and slow axes. However, the focus lens 96 is configured to form different focal lengths for the fast axis and the slow axis. In the present embodiment, the focal length of the slow axis is configured to be greater than the focal length of the fast axis.

The focus lens 96 comprises a first focus lens portion 96a and a second focus lens portion 96b. The first focus lens portion 96a is spherical and is configured to focus the laser beam 94 along both its fast and slow axes. The second focus lens portion 96b is cylindrical and is configured to focus the laser beam 94 along one of its fast or slow axes only. Alternatively, the first and second focus lens portions 96a, 96b are both cylindrical, with one of the lens portions focusing the fast axis of the laser beam 94 only, and the other lens portion focusing the slow axis of the laser beam 94 only.

The head unit 90 has a cutting zone 97 in which hairs are received to be cut. The laser generator 92 is disposed on one side of the cutting zone 97. A first window 98a is disposed between the cutting zone 97 and the focus lens 96. A second window 98b is disposed at the other end of the cutting zone 97 to the first window 98a. However, it will be understood that the windows 98a, 98b may be omitted. The cutting head 90 further comprises a body with a spacer 102 that contacts a section of the skin of a user to maintain protective separation between the laser beam 94 and the skin.

A focusing element 91 forming part of the optical system 93 is disposed in the cutting zone 97. The focusing element 31 is incident with the optical axis of the laser beam 94. The focusing element 91 is configured to refocus the laser beam 94 passing through the cutting zone 97. The focusing element 91 is a refractive lens. The focusing element 91 is a cylindrical lens.

The focusing element 91 is configured to focus the laser beam 94 along its fast axis. The fast axis extends along the x-axis. The slow axis of the laser beam 94 is not refocused by the focusing element 91.

The laser beam 94 in the cutting zone 97 will conform to Gaussian theory along its fast and slow axes. The focus lens 96 causes the laser beam 94 to converge along its fast axis (y-axis) and its slow axis (x-axis) as the beam extend along its optical axis. The first focus lens portion 96a defines the focal length of the laser beam along its slow axis. The second focus lens portion 96b defines the focal length of the laser beam along its fast axis. The focal length of the laser beam along its slow axis is greater than the focal length of the laser beam along its fast axis. Therefore, the focal points of the laser beam 94 along its slow and fast axes are offset from each other.

The laser beam 94 will have a 'first fast axis focal point' 99, or waist, located along its optical axis. The high intensity region at the first focal point 99 along its fast axis, together with the regions immediately on each side of the high intensity region, define an effective cutting area. That is, the section of the laser beam 94 which has effective cutting characteristics to cut hair.

When the laser generator 92 is operated, the emitted laser beam 94 is focused by the focus lens 96. The slow axis of the laser beam 94 is focused by the first focus lens portion 96a. The fast axis of the laser beam 94 is focused by the second focus lens portion 96b. The focusing element 91 is disposed in a middle section 97a of the cutting zone 97. The laser beam 94 travels through a first outer section 97b of the cutting zone 97.

The first fast axis focal point 99 is in the first outer section 97b. A first effective cutting area of the laser beam 94 is therefore formed in the first outer section 43b. The laser beam also has a 'slow axis focal point' 101. As explained above, the slow axis focal point 101 is offset from the first fast axis focal point 99. The focus lens 96 and the focusing element 91 are spaced apart from each other and positioned so that the slow axis focal point 101 coincides with the focusing element 91. Therefore, when the laser generator is operated the slow axis is symmetrical either side of the focusing element 91.

The laser beam 94 is then re-focused by the focusing element 91. The laser beam 94 is refocused by the focusing element 91 along the fast axis (y-axis) only. A second focal point 100 of the laser beam 94 is formed in the second outer section 97c. A second effective cutting area of the laser beam 94 is formed in the second outer section 97c. As the slow axis focal point 101 of the laser beam 94 coincides with the focusing element 91, it begins to diverge away from the focusing element 91 in the second outer section 97c of the cutting zone 97. However, it will be understood that the laser beam 94 diverges along its slow axis in the second outer section 97c at substantially the same rate as it converged in the first outer section 97b. Therefore, the dimensions, and the power density, of the laser beam 94 at the first and second fast axis focal points 99, 100 correspond with each other.

Figure 10:
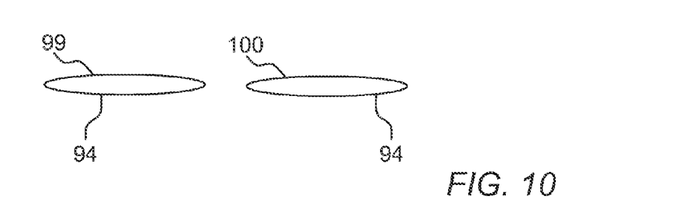
FIG. 10 shows a cross-sectional view of a laser beam of the embodiment of a device for cutting hair shown in FIGS. 8 and 9 along the optical axis of the laser beam at first and second focal points.

A cross-sectional view of the laser beam 94 at the first and second focal points 99, 100 is shown in FIG. 10. The laser beam 94 has corresponding dimensions along both its x-axis and y-axis at the first and second focal points 99,100.

The laser beam 94 subsequently passes from the cutting zone 97 and travels away from the cutting zone 97 to be absorbed within the energy dissipater or similar device (not shown) to prevent damage being caused by the energy of the remaining laser beam 94.

In the embodiment described above, with reference to FIGS. 8 to 10, the focal length of the slow axis is greater than the focal length of the fast axis so that the focal point of the slow axis is offset from the focal point of the fast axis. This means that the width of the beam along the slow axis can be the same at both the first and second focal points of the fast axis when a focusing element is used to extend the effective cutting area of the laser beam. However, it has been found that an optical system configured to have different focal lengths along each of the fast and the slow axes may be used to extend the effective cutting area of the laser beam without a focusing element disposed in the cutting zone. It will be understood that the arrangements and features in the embodiments described below can be used together with and in combination with the arrangements and features described above. In particular, a focusing element may be used together with the arrangement described below with reference to FIGS. 11 and 12.

Figure 11:
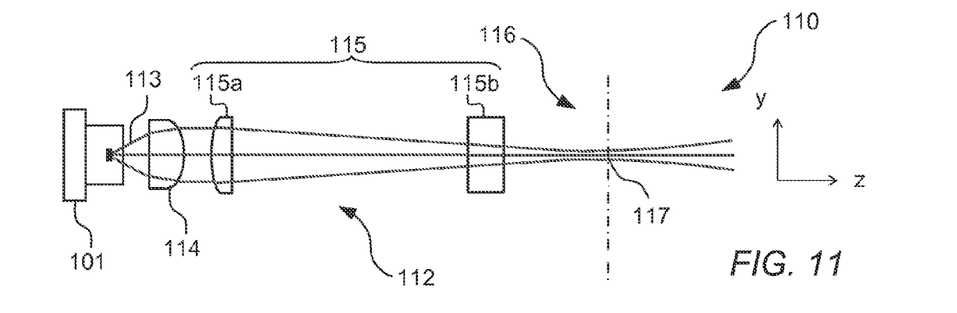
FIG. 11 shows a schematic side view of a cutting head of another embodiment of a device for cutting hair.
Figure 12:
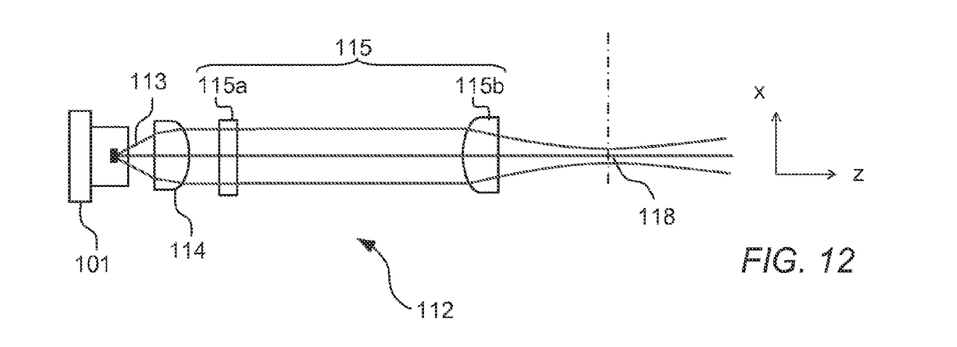
FIG. 12 shows a schematic plan view of the cutting head shown in FIG. 11.

Referring to FIGS. 11 and 12, another embodiment of a cutting head 110 for cutting hair is shown. The head unit 110 comprises a laser generator 111, acting as a laser source, and an optical system 112. The laser generator 111 emits a laser beam 113. The laser beam 113 follows an optical path in the head unit 110 from the laser generator 111 along an optical axis.

The emitted laser beam 113 is directed towards the optical system 112. The optical system 112 has a collimating lens 114 and a focus lens 115. The laser beam 113 is directed towards the collimating lens 114. The collimating lens 114 reduces or eliminates the divergence of the beam. The laser beam 113 is then focused by the focus lens 115 to cause the beam 113 to converge.

The focus lens 115 is configured to focus the laser beam 113 along both its fast and slow axes. However, the focus lens 115 is configured to form different focal lengths for the fast axis and the slow axis. In the present embodiment, the focal length of the fast axis is configured to be greater than the focal length of the slow axis.

The focus lens 115 comprises a first focus lens portion 115a and a second focus lens portion 115b. The first focus lens portion 115a is cylindrical and is configured to focus the laser beam 113 along its fast axis. The first focus lens portion 115a is disposed proximate the collimating lens 114. The second focus lens portion 115b is cylindrical and is configured to focus the laser beam 113 along its slow axis. In the present arrangement, the first and second focus lens portions 115a, 115b are refractive lenses.

The head unit 110 has a cutting zone 116 in which hairs are received to be cut. The laser generator 101 is disposed on one side of the cutting zone 116. The focus lens 115 is disposed on the same side of the cutting zone 116. The cutting head further comprises a body (not shown) with a spacer (not shown) that contacts a section of the skin of a user to maintain protective separation between the laser beam 113 and the skin.

The laser beam 113 in the cutting zone 116 will conform to Gaussian theory along its fast and slow axes. The focus lens 115 causes the laser beam 113 to converge along its fast axis (y-axis) and its slow axis (x-axis) as the beam 113 extends along its optical axis. The first focus lens portion 115a defines the focal length of the laser beam 113 along its fast axis. The second focus lens portion 115b defines the focal length of the laser beam along its slow axis.

The laser beam 113 will have a 'fast axis focal point' 117, or waist, located along its optical axis. The high intensity region at the fast axis focal point 117, together with the regions immediately on each side of the high intensity region, define an effective cutting area. That is, the section of the laser beam 113 which has effective cutting characteristics to cut hair. The laser beam 113 will also have a 'slow axis focal point' 118, or waist, located along its optical axis.

The first focus lens portion 115a is spaced from the second focus lens portion 115b. It will be understood that the spacing of the first focus lens portion 115a from the second focus lens portion 115b will determine the distance between the fast axis focal point 117 and the slow axis focal point 118. In the present embodiment, the fast axis focal point 117 and the slow axis focal point 118 are aligned with each other. That is, the focal points 117, 118 of the fast axis and the slow axis coincide with each other. This provides a symmetrical cutting action across the length of the cutting zone 116.

The focal length of the laser beam along its fast axis is greater than the focal length of the laser beam along its slow axis. This means that the laser beam 113 has a low numerical aperture along its fast axis (refer to FIG. 11), and a high numerical aperture along its slow axis (refer to FIG. 12). This means that the size of the high intensity region is maximised.

The laser beam width or diameter along the slow axis (dimension along the x-axis) at the focal point is determined by the near field of the laser beam and the magnification of the optical system 112, and is given by:

$$\phi_s = d_s \frac{f}{f_c},$$

Wherein:
  $\phi_s$ is the diameter of the laser beam in focus along the slow axis;
  $d_s$ is the diameter of the near field of the laser in the slow axis;
  f is the focal length of the focus lens; and
  $f_c$ the focal length of the collimator.

The minimum beam diameter in focus along the slow axis (dimension along the x-axis) is determined by the diffraction limit:

$$\phi_f = \frac{4\lambda \cdot f}{\pi \theta \cdot f_c},$$

Wherein:
  $\lambda$ is the wavelength of the laser; and
  $\theta$ is the fast axis divergence angle of the laser beam (in radians).

Figure 13:
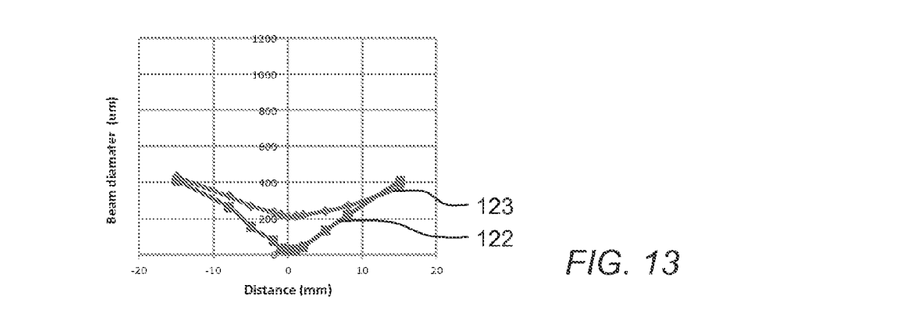
FIG. 13 is a chart showing the width of the laser beam, or beam diameter, against the distance from the focal point of the laser beam for an optical system of the cutting head shown in FIGS. 11 and 12.
Figure 14:
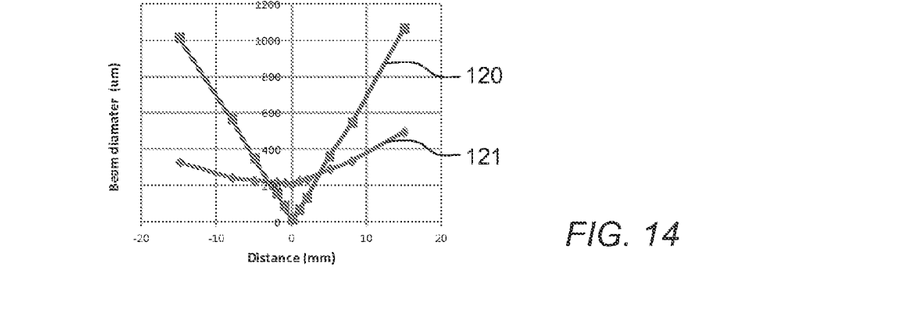
FIG. 14 is a chart showing the width of the laser beam, or beam diameter, against the distance from the focal point of the laser beam for an optical system having a spherical focus lens.

An example simulation of the above described arrangement is shown in FIG. 13, and a comparison example simulation of another arrangement having a spherical focus lens as the focus lens is shown in FIG. 14.

FIG. 13 shows the width of the laser beam, or beam diameter, against the distance from the focal point of the laser beam for the exemplary embodiment described above with reference to FIGS. 11 and 12.

In the exemplary embodiment described above, the fast axis focus lens portion 115a has a focal length of 75 mm and the slow axis focus lens portion 115b has a focal length of 30 mm. The focal length of the collimating lens is 2.97 mm. The laser generator 101 emits a laser beam having a wavelength of 450 nm, a far field slow axis beam divergence of 12°, and a fast axis beam divergence of 44° ($1/e^2$, full angle). The dimension of the near field along the y-axis is 2.1 μm. The dimension of the near field along the x-axis is 18.3 μm. It will be understood that although specific dimensions are given, other alternative dimensions are envisaged.

FIG. 14 shows the width of the laser beam, or beam diameter, against the distance from the focal point of the laser beam for an optical system having a spherical focus lens. The spherical focus lens has a focal length of 30 mm. It is clear from FIG. 14 that the dimensions of the laser beam along the fast axis 120 and the slow axis 121 at ±15 mm defocus (i.e. 15 mm from the focal point of the laser beam) for the optical system with a spherical focus lens are relatively large, in particular for the fast axis, which results in a poor cutting efficiency. However, with the arrangement having a fast axis focus lens portion 115a having a focal length of 75 mm and a slow axis focus lens portion 115b having a focal length of 30 mm the dimensions of the laser beam at ±15 mm defocus are comparable with the dimensions of the laser beam of the spherical focus lens having a focal length of 30 mm at ±5 mm defocus.

This means that the power density at the ends of a cutting zone having a length of 30 mm for the embodiment described above would have a power density which is similar to the power density of a cutting zone having a length of 10 mm when a spherical focus lens is used.

The laser beam 113 subsequently passes from the cutting zone 116 and travels away from the cutting zone 116 to be absorbed within the energy dissipater or similar device (not shown) to prevent damage being caused by the energy of the remaining laser beam 113.

It will be appreciated that each of the cutting heads described above may be a separate cutting head unit that is attachable to a shaver handle. The cutting head unit may be removed to clean the cutting head or to replace the cutting head or components of the cutting head after they have become worn. The cutting heads may be interchangeable. Alternatively, the cutting head may be integrated with a shaver handle as one product (not shown).

Although in the above described embodiments the laser generator is disposed in the cutting head, it will be understood that in an alternative arrangement the laser generator is disposed in a shaver handle to which the cutting head is mountable. With such an arrangement, a mounting unit is provided to ensure that the laser generator is aligned with the optical system in the cutting head.

The above-described cutting heads relate to shaving the skin to achieve a minimum remaining hair length as well as improved uniformity of remaining hair length. However, it will be understood that the cutting heads may alternatively be used for trimming hair to a controlled length that is not necessarily as short as possible, as is the case with a hair trimming or grooming device. To achieve this, the guard would be positioned further from the cutting laser beam(s) so that the cutting height is increased, but remains uniform.

Although in the above described embodiments, the optical system is shown configured so that the laser beam follows a linear path, it will be understood that in an alternative arrangement reflective elements may be disposed to reflect the laser beam. This enables the size of the cutting head to be minimised.

In the above described embodiments, separate focus lenses and collimating lenses are used. However, it will be understood that two or more of these lenses may be integrally formed with each other.

In the above-described embodiments the head unit is shown with the laser beam following a generally linear path. However, it will be understood that the path of the laser beam may be redirected through the optical system having one or more reflective elements. For example, with the embodiments described above a first reflective element may be disposed to direct a laser beam generated by the laser generator across the cutting zone. With such an arrangement, a second reflective element may be positioned on the opposite side of the cutting zone to reflect the laser beam along an exit section or path that travels away from the cutting zone.

A reflecting element may be disposed on one side of the cutting zone to reflect the laser beam back across the cutting zone, to create a second cutting section of the beam that passes through the cutting zone, therefore improving the cutting performance of the shaver. The second cutting section of the beam may be reflected along a second optical axis in the cutting zone such that there are two parallel adjacent sections of the laser beam extending across the cutting zone. Alternatively, the second cutting section of the beam may be at an angle to the first cutting section of the beam. The one or more focusing elements may be located either before or after such a reflecting or refractive element.

Optionally, additional subsequent reflecting elements (not shown) may be used to reflect the laser beam back across the cutting zone multiple times, allowing the beam to pass for a third, fourth and fifth times across the cutting zone.

With the above arrangements it is possible to achieve a smaller intensity variation of a laser beam along their length. This enables the size of the cutting area to be maximised whilst minimising the power of the laser generator. Although Gaussian laser beams have a natural divergence along their length, the above embodiments provide a means of maximising the distributed intensity along their length, and so minimise uneven hair severing and non-uniform closeness.

It will be appreciated that the term "comprising" does not exclude other elements or steps and that the indefinite article "a" or "an" does not exclude a plurality. A single processor may fulfill the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A cutting head for a device for cutting hair, comprising:
an optical system configured to direct a laser beam having a fast axis and a slow axis across a cutting zone in the cutting head,
the optical system comprising a focus lens configured to form a first focal point of the laser beam in the cutting zone,
and a focusing element configured to form a second focal point of the laser beam in the cutting zone.

2. A cutting head according to claim 1, wherein the focusing element is in the cutting zone.

3. A cutting head according to claim 1, wherein the focusing element is a refractive lens or a reflective lens.

4. A cutting head according to claim 1, wherein the focusing element is a cylindrical lens.

5. A cutting head according to claim 4, wherein the focusing element is configured to refocus the laser beam along its fast axis only.

6. A cutting head according to claim 5, wherein the focusing element is configured to focus at least two laser beams.

7. A cutting head according to claim 6, wherein the focus lens is configured to form a focal point of the laser beam along its fast axis which is offset from a focal point of the laser beam along its slow axis.

8. A cutting head according to claim 7, wherein the focus lens is configured to form a focal length of the laser beam along its fast axis which is greater than the focal length of the laser beam along the slow axis.

9. A cutting head according to claim 8, wherein the focusing element is a first focusing element, and the cutting head further comprises a second focusing element configured to refocus the laser beam along its fast and/or slow axis.

10. A cutting head for a device for cutting hair, comprising:
an optical system configured to direct a laser beam having a fast axis and a slow axis across a cutting zone in the cutting head,
the optical system comprising a focus lens configured to form a focal length of the laser beam in the cutting zone along its fast axis which is greater than a focal length of the laser beam in the cutting zone along its slow axis.

11. A cutting head according to claim 10, wherein the focal length of the laser beam along the fast axis is at least double the focal length of the laser beam along the slow axis.

12. A cutting head according to claim 10, wherein the focus lens is configured so that a focal point of the laser beam along the fast axis coincides with a focal point of the laser beam along the slow axis.

13. A cutting head according to claim 10, wherein the focus lens comprises a first focus lens portion configured to focus the laser beam along its fast axis and a second focus lens portion configured to focus the laser beam along its slow axis.

14. A cutting head according to claim 10, wherein the optical system further comprises a collimating lens, the first focus lens portion and the collimating lens being integrally formed.

15. A cutting head according to claim 10, further comprising a focusing element configured to form a second focal point along the slow axis and/or the fast axis of the laser beam in the cutting zone.

* * * * *